United States Patent
Welshans

(10) Patent No.: US 7,032,537 B2
(45) Date of Patent: Apr. 25, 2006

(54) METHOD AND HOUSING ASSEMBLY FOR FARMING MEMBERS OF THE PHYLUM ARTHROPODA

(76) Inventor: Wendy L. Welshans, P.O. Box 73, West Cornwall, CT (US) 06796

( * ) Notice: Subject to any disclaimer, the term of this patent is extended or adjusted under 35 U.S.C. 154(b) by 0 days.

(21) Appl. No.: 11/244,935

(22) Filed: Oct. 6, 2005

(65) Prior Publication Data

US 2006/0027172 A1    Feb. 9, 2006

Related U.S. Application Data

(62) Division of application No. 10/711,284, filed on Jun. 1, 1999.

(60) Provisional application No. 60/501,355, filed on Sep. 9, 2003.

(51) Int. Cl.
*A01K 29/00* (2006.01)
(52) U.S. Cl. .................................................. 119/6.5
(58) Field of Classification Search ................ 119/436, 119/437, 444, 445, 482, 487, 270, 6.5, 493, 119/428, 416, 429, 448, 489, 490, 491, 500, 119/161, 165, 706, 6.6, 6.7; 449/3, 15, 46, 449/13; 43/107, 113
See application file for complete search history.

(56) References Cited

U.S. PATENT DOCUMENTS

| 2,331 A | 11/1841 | Tillinghast |
|---|---|---|
| 663,916 A | 12/1900 | Markwell |
| 2,416,037 A | 2/1947 | Mead |
| 2,593,296 A | 4/1952 | Green |
| 3,468,289 A | 9/1969 | Brodia |
| 3,721,052 A | 3/1973 | Boel et al. |
| 3,727,580 A | 4/1973 | Yumlyama et al. |
| 3,762,372 A | 10/1973 | Mente et al. |
| 4,716,609 A | 1/1988 | Norman |
| 5,002,013 A | 3/1991 | Brown |
| 5,247,901 A | 9/1993 | Landon et al. |
| 6,129,051 A | 10/2000 | Jessie et al. |
| 6,145,477 A | 11/2000 | Jansen |

*Primary Examiner*—Son T. Nguyen
(74) *Attorney, Agent, or Firm*—Howard & Howard

(57) ABSTRACT

A method and a housing assembly (10) for farming members of the Phylum Arthropoda (12) to collect silk therefrom in a centralized location without the members exhibiting territoriality tendencies is disclosed. The housing assembly (10) includes a wall (22) defining a plurality of frames (24) in close proximity with one another and disposed about a work space (26). Each frame (24) presents an open frame space (28) having a predetermined area and the work space (26) has a foot print (30) of a predetermined area such that a ratio is established therebetween. The ratio of the predetermined area of the open frame space (28) to the predetermined area of the foot print (30) is at least 1:5. A roof (32) is supported by the wall (22) for covering the frames (24) and the work space (26) and has an eave (34) that extends perpendicularly beyond the wall (22) a predetermined distance to protect the frames (24).

7 Claims, 3 Drawing Sheets

METHOD AND HOUSING ASSEMBLY FOR FARMING MEMBERS OF THE PHYLUM ARTHROPODA

RELATED APPLICATIONS

This application is a divisional of application Ser. No. 10/711,284 filed on Sep. 8, 2004 which claims priority to U.S. provisional patent application having Ser. No. 60/501,355, which was filed on Sep. 9, 2003.

BACKGROUND OF THE INVENTION

1. Field of the Invention

A method and a housing assembly for farming members of the Phylum Arthropoda in a centralized location to collect silk therefrom.

2. Description of the Related Art

Members of the Phylum Arthropoda, especially referring to spiders, are able to dispense different types of silk from their bodies. The various types of silk are used by the spiders for different purposes. For example, one type of silk excreted from the ampullate glands is commonly referred to as a dragline and is used when the spider ventures from its web. The dragline is stronger than the other types of silk and the spider can climb back up the dragline if there is danger. The various types of silk have specific properties that make them useful for various applications, such as medical, pharmaceutical, or commercial applications. One medical application may use the silk for sutures because the silk is antibacterial and biodegradable, while also having very good tensile properties. The silk may also be used as artificial ligaments and to reinforce torn tendons. One commercial application may incorporate the silk into garments for replacing Kevlar vests currently used in ballistic protection.

However, extracting the silk from the spiders has been difficult. It requires large numbers of spiders to produce a large quantity of the silk to be commercially practical. Therefore, other methods of making the silk have been researched instead of collecting the silk directly from the spiders. One method has been to genetically alter goats so that the milk produced by the goat includes enzymes used to fabricate the silk. The enzymes are extracted from the goat's milk and then the silk is made from the extracted enzymes. Other methods have employed bacteria and the like to produce the enzymes for combining to make the silk. The silk made by these methods is useable; however, the silk typically does not have the same physical properties as the silk directly extracted from the spiders.

Various related art references disclose that it is impractical to collect the silk directly from the spiders. The silk produced by the spiders has a thickness of about 1/100th of the thickness of a human hair and therefore many spiders must be used to collect large amounts of silk. It is known by those skilled in the art that the spiders are very territorial and exhibit cannibalistic tendencies when housed in close proximity with one another. Moreover, the references state that when many spiders are left together, only one will remain, as it will have killed the other spiders.

In order to farm the spiders, current methods employ separate cages that keep the spiders separate from one another. However, it has been discovered that the silk produced by the spiders in captivity does not produce the same high quality silk as produced by spiders in their natural environment. It is believed that housing the spiders in enclosed, separate cages increases the stress of the spiders and the increased stress results in the silk having inferior physical properties relative to silk produced from spiders in their natural environment.

SUMMARY OF THE INVENTION

The invention provides a method and a housing assembly for farming members of the Phylum Arthropoda in a centralized location to collect silk therefrom. The assembly comprises a wall defining a plurality of frames and establishing an outer periphery defining a work space having a foot print of a predetermined area. Each of the frames defines an open frame space having a predetermined area for housing the members of Phylum Arthropoda to create a web therein. A roof is supported by the wall for covering the frames and the work space. The assembly is characterized by a ratio of the predetermined area of the open frame space to the predetermined area of the foot print of at least 1:5 to prevent territoriality of the members of Phylum Arthropoda.

The method of farming members of the Phylum Arthropoda comprises the steps of disposing the frames about the work space, covering the frames and the work space for protection from exterior environmental conditions, and disposing a member of the Phylum Arthropoda in each of at least two different frames for building webs within the open frame spaces. A food supply is attracted into the open frame space from the exterior environment and the silk is harvested from the members of the Phylum Arthropoda.

The silk collected from the members farmed in the housing assembly of the subject invention has properties and characteristics similar to that of the silk produced by spiders in their natural environment. The subject invention provides adequate space to reduce the stress of the members even though they are in captivity. The space is also adequate to prevent territoriality and cannibalistic tendencies of the members, while also creating a self-sustaining environment for collecting silk.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE PREFERRED EMBODIMENT

Figure 1:
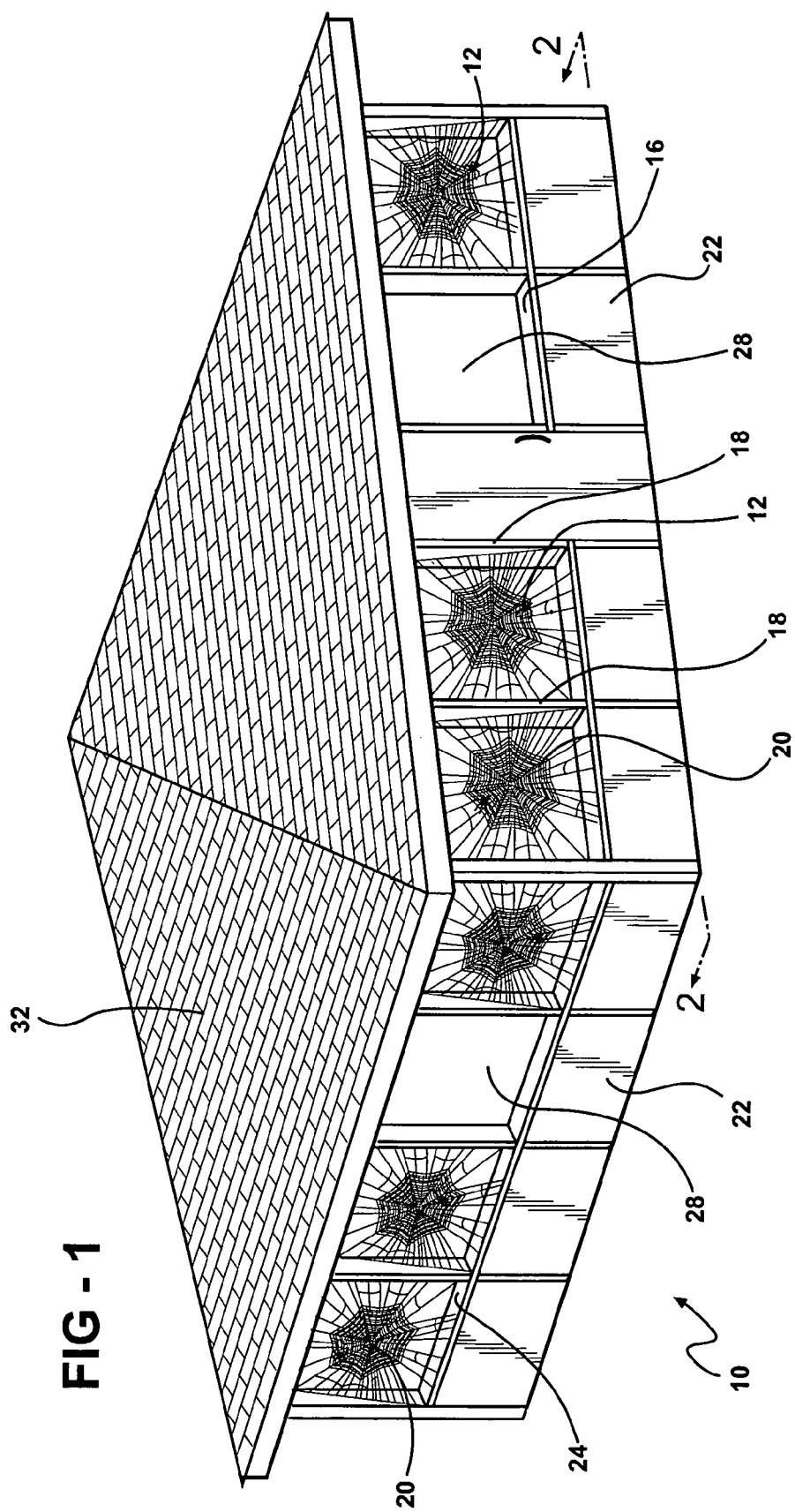
FIG. 1 is a perspective exterior view of a housing assembly for farming members of the Phylum Arthropoda.

The subject invention provides a method and a housing assembly for farming members of the Phylum Arthropoda 12 to collect silk therefrom shown generally at 10 in FIG. 1. The assembly 10 allows the members 12 to be housed in a centralized location without the members exhibiting territoriality tendencies. Specifically, the members of the Phylum Arthropoda 12 are members of the Order Araneae (Arachnida). The order of Arachnida includes spiders, all having a body divided into a cephalothorax and a short usually unsegmented abdomen, a chelicerae modified into poison fangs, leg-like pedipalpi, simple eyes, a web-spinning apparatus at the end of the abdomen, and respiratory lung sacs or tracheae in the abdomen. Preferably, the members are from the Family Araneidae and the Genus *Nephila*. The Family Araneidae includes spiders that spin elaborate webs 20 and including over 2,500 species. The spiders vary greatly in size; some species of *Singa* are about 2 mm in length, while some of the *Nephila* can grow to over 45 mm. In the most preferred embodiment, the member of the Genus *Nephila* is a *Nephila Clavipes* (*N. clavipes*) spider. For clarity, the subject invention will be described with reference to *N. clavipes* or spiders without being limited thereto.

The *N. clavipes* spiders are preferably farmed in the regions, which they are commonly found. The *N. clavipes* spiders are found in the southeast regions of the United States through Argentina and Peru. The *N. clavipes* spider is most commonly found in Puerto Rico. Farmers in these regions are continually cutting down the rain forests for their livestock. However, these farmers could shift their resources from clearing the forests to farming the *N. clavipes* spiders due to the potential profitability of harvesting the *N. clavipes* spider silk as a valuable resource.

Figure 2:
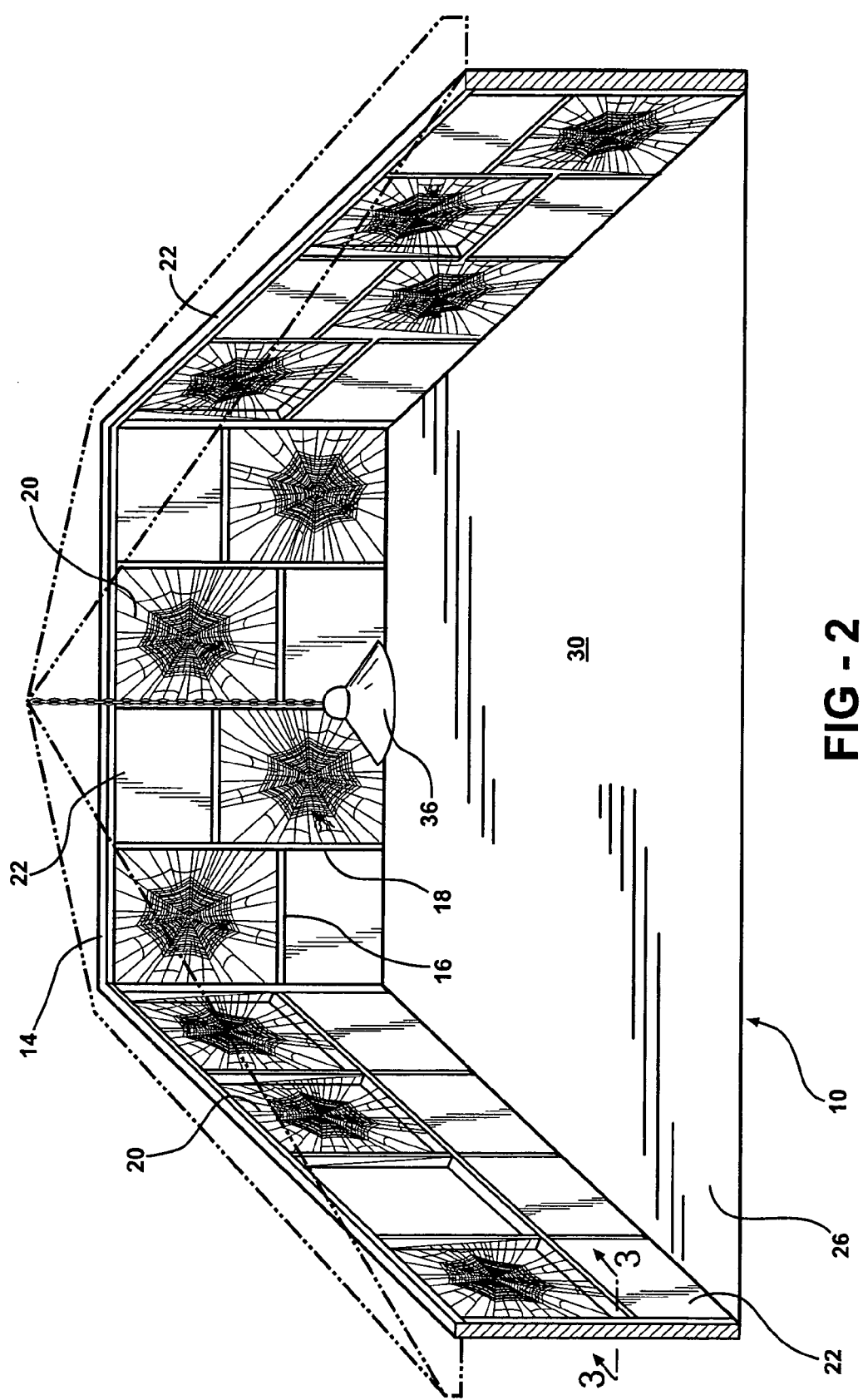
FIG. 2 is a perspective interior view of the housing assembly taken along line 2—2 in FIG. 1.
Figure 3:
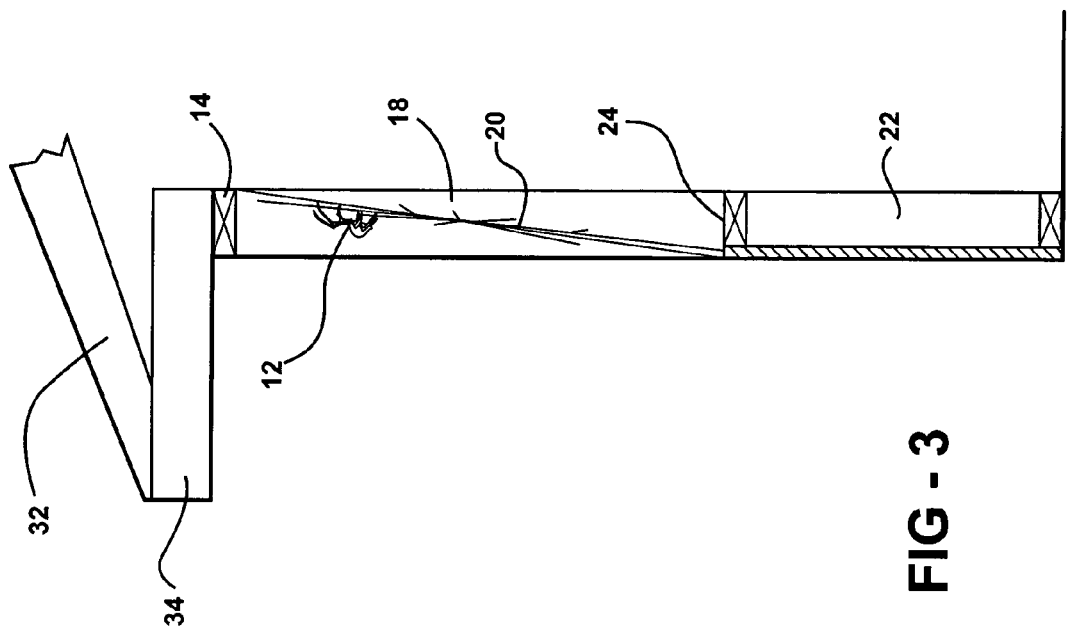
FIG. 3 is a cross-sectional view of a wall taken along line 3—3 in FIG. 2.

Referring to FIGS. 1–3, the housing assembly 10 includes a wall 22 defining a plurality of frames 24 in close proximity with one another and disposed about a work space 26. Each frame 24 presents an open frame space 28 having a predetermined area and the work space 26 has a foot print 30 of a predetermined area. *N. clavipes* spiders are disposed in each of at least two different frames 24 for building webs 20 within the open frame space 28. Said another way, there is only one spider per frame 24 and there are many spiders within the work space 26 each having their own frame 24.

As shown in FIG. 3, the spiders build three-dimensional webs 20 spanning portions of the frames 24. Referring to back FIG. 2, the frames 24 are shown adjacent one another and in a straight line on the wall 22 to the left of the work space 26. Alternatively, the frames 24 may also be disposed diagonally to one another to give the spiders more area, as shown on the other walls 22.

The assembly is characterized by a ratio of the predetermined area of the open frame space 28 to the predetermined area of the foot print 30 of at least 1:5. The areas are best illustrated in FIG. 2. As an example, when the predetermined area of the open frame space 28 is nine square feet, then the predetermined area of the foot print 30 should be at least forty-five square feet. The ratio is important to prevent territoriality of the members of Phylum Arthropoda. Establishing such a ratio allows the spiders to build their webs 20 without infringing on neighboring frames 24 and inciting the territoriality tendencies of the spiders. This allows the spiders to be housed in a central location and farmed which has previously been thought unobtainable since the spiders are cannibalistic. Preferably, the ratio of the predetermined area of the open frame space 28 to the predetermined area of the foot print 30 is as at least 1:9.

In a preferred embodiment, the predetermined area of the open frame space 28 is at least four square feet. The frames 24 may further comprise a top member 14, a bottom member 16, and side members 18 and the frames 24 are generally rectangular shaped. Other geometrical shapes may be used having less than or more than four sides, such as, but not limited, triangular, circular, or hexagonal, so long as the ratio of the areas is satisfied. Preferably, when the frames 24 are rectangular shaped, the side members 18, the top member 14, and the bottom member 16 are each at least three feet long.

The predetermined area of the foot print 30 is preferably at least seventy-five square feet. The foot print 30 may be any geometrical shape so long as the ratio of the areas may be established. Preferably, the foot print 30 is rectangular and the predetermined area of the foot print 30 is at least ten feet by ten feet. However, the foot print 30 may be other shapes, such as circular or octagonal without deviating from the subject invention.

In one embodiment, the wall 22 comprises a plurality of walls establishing the outer periphery. Each of the walls 22 has at least one frame 24 defined therein, and more preferably a plurality of frames 24 are defined therein. When the foot print 30 is rectangular shaped, there are four walls 22 defining the work space 26, whereas if the foot print 30 was circular, then there would be a single wall 22. The most preferred embodiment has the walls 22 that are each twelve feet long such that the work space 26 has the predetermined area of one-hundred forty four square feet. The frames 24 in this embodiment are four feet by four feet having the predetermined area of sixteen square feet. The ratio of the area of the frames 24 to the area of the work space 26 is 1:9.

Referring again to FIG. 3, the frames 24 and the work space 26 are covered for protection from exterior environmental conditions, such as rain and wind. Since the frames 24 and the work space 26 are covered, an environment is created for the spiders such that the spiders have no reason to leave the frames 24. Also, since the frames 24 are spaced far enough from one another to prevent territoriality, the spiders are less stressed and will produce high quality silk to be harvested. The frames 24 and the work space 26 are covered by a roof 32 supported by the wall 22. The roof 32 includes eaves 34 that extend perpendicularly beyond the wall 22 a predetermined distance. In order to protect the webs 20 created within the frames 24, the eaves 34 preferably extend perpendicularly at least two feet beyond the wall 22. More preferably, the eaves 34 extend perpendicularly from two to three feet. The roof 32 may have various pitches, so long as the eaves 34 extend perpendicularly from the wall 22 at least two feet.

With reference back to FIG. 2, a light source 36 is disposed within the work space 26 for drawing a food source through the open frame space 28 and into the web 20 from the exterior environment. The food source may be any type of insect and is preferably those insects that are naturally occurring in the environment where the housing assembly 10 is located. When the light source 36 is activated, the food source is drawn into the work space 26 through the open frame space 28 and is caught in the webs 20. Catching the food source in the webs 20 acts as a natural food source for the spiders and is yet another reason that the spiders do not defect from the housing assembly 10. However, those skilled in the art recognize that the spiders may also be fed by hand. The food sources may include insects selected from the following orders of Insecta: Orthoptera, Lepidoptera, Coleoptera, Diptera, Hymenoptera.

Figure 4:
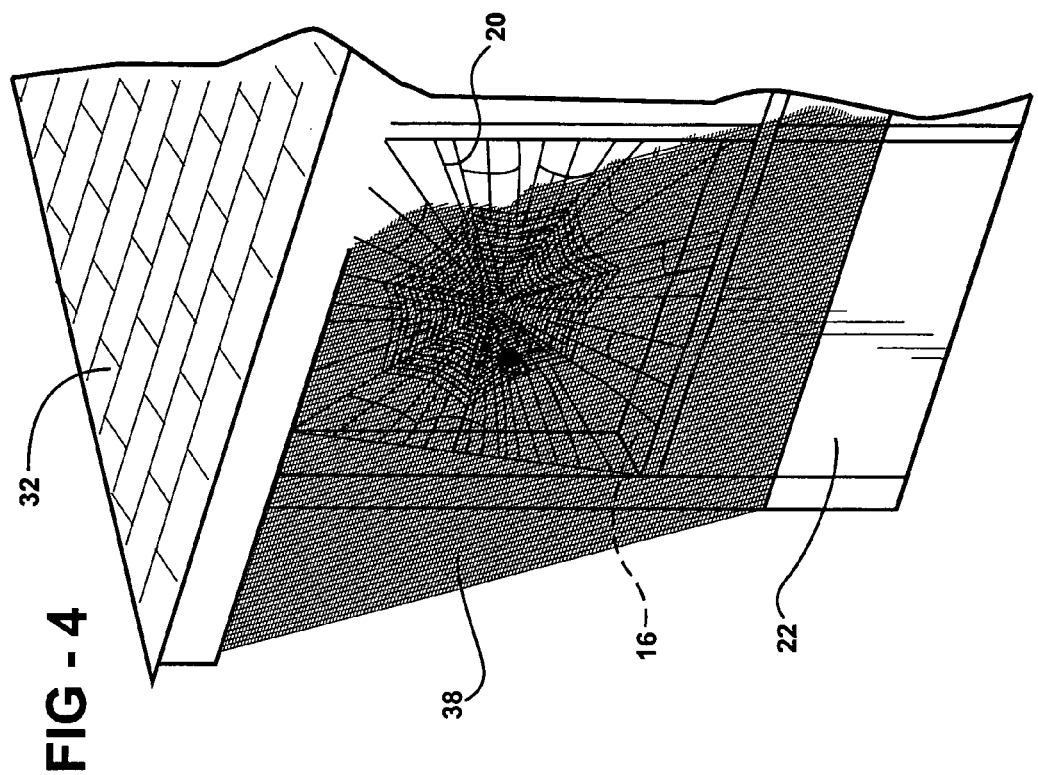
FIG. 4 is a close-up perspective view of an alternate embodiment of the housing assembly including a netting.

Another embodiment of the housing assembly 10 is illustrated in FIG. 4. Even though the spiders have adequate space, protection, and food source, a netting 38 may be used to removably cover the frames 24. The netting 38 would be loosely positioned adjacent the exterior of the frames 24 for limiting defection of the members therefrom. The netting 38 allows the spiders to move about the work space 26, while preventing the spiders from leaving the housing assembly 10. Since farming the spiders may include a significant investment to collect the spiders, the netting 38 serves to protect the spiders from natural predators. The netting 38 is removable to allow the food source to be attracted through the open frame spaces 28 and then the netting 38 would be replaced. Using such a netting 38 does not cause the spiders stress and as such, the silk that is obtained has good physical properties.

The centralized housing assembly 10 is particularly well suited for harvesting silk from the members of the Phylum Arthropoda 12. One such method of harvesting silk is disclosed in U.S. Pat. No. 6,412,261, which is incorporated herein by reference. The member of the Phylum Arthropoda is removed from the open frame space 28 and silk is withdrawn. After the silk has been withdrawn, the spider is returned to the web 20 in the open frame space 28 to recover and to prepare for the next harvesting. Using such a housing assembly 10 and method as disclosed herein, silk can be extracted from the spiders at rates of about 4,000 feet per 7.4 hours for each of the spiders. Therefore, the collection of the silk directly from the spiders becomes practical when employing the subject invention. Moreover, since the other related art methods discussed above have yet to achieve spider silk with the same properties as naturally occurring spider silk, the subject invention has achieved the farming of spiders which has previously been thought not possible.

Obviously, many modifications and variations of the present invention are possible in light of the above teachings. The invention may be practiced otherwise than as specifically described within the scope of the appended claims, wherein that which is prior art is antecedent to the novelty set forth in the "characterized by" clause. The novelty is meant to be particularly and distinctly recited in the "characterized by" clause whereas the antecedent recitations merely set forth the old and well-known combination in which the invention resides. These antecedent recitations should be interpreted to cover any combination in which the incentive novelty exercises its utility. In addition, the reference numerals in the claims are merely for convenience and are not to be read in any way as limiting.

What is claimed is:

1. A method of farming members of the Order Araneae (12) in a centralized location without exhibiting territoriality tendencies, said method comprising the steps of:

disposing a plurality of frames (24) about a work space (26), with each frame (24) presenting an open frame space (28) and in close proximity with one another;

covering the frames (24) and the work space (26) for protection from exterior environmental conditions;

disposing a member of the Order Araneae (12) in each of at least two different frames (24) for building webs (20) within the open frame space (28);

disposing a light source (36) within the work space (26) to attract a food supply into the open frame space (28) from the exterior environments, activating the light source (36) for drawing the food source through the open frame space (28); and harvesting silk from the members of the Order Araneae (12).

2. A method as set forth in claim 1 wherein the step of disposing the member of the Order Araneae is further defined disposing a member of the Genus *Nephila* in the frames (24).

3. A method as set forth in claim 2 wherein the step of disposing the member of the Genus *Nephila* is further defined as disposing a *Nephila Clavipes* spider in the frames (24).

4. A method as set forth in claim 1 further comprising the step of activating the light source (36) for drawing the food source through the open frame space (28).

5. A method as set forth in claim 1 wherein the step of harvesting silk further comprises the step of removing the member of the Order Araneae (12) from the open frame space (28) and withdrawing silk from the member of Order Araneae (12).

6. A method as set forth in claim 5 further comprising the step of disposing a netting (38) over the open frame space (28) for limiting defection of the member of the Order Araneae (12) from the work space (26).

7. A method as set forth in claim 1 wherein the step of disposing the frames (24) about the work space (26) is further defined as disposing the frames (24) about the work space (26) having a ratio of a predetermined area of the open frame space (28) to a predetermined area of a foot print (30) of the work space (26) of at least 1:5 to prevent territoriality of the members of Order Araneae (12).

* * * * *

UNITED STATES PATENT AND TRADEMARK OFFICE
CERTIFICATE OF CORRECTION

PATENT NO. : 7,032,537 B2  Page 1 of 1
APPLICATION NO. : 11/244935
DATED : April 25, 2006
INVENTOR(S) : Wendy Welshans It is certified that error appears in the above-identified patent and that said Letters Patent is hereby corrected as shown below:

Column 6, Line 7: Replace "a food supply" with --a food source--.

Column 6, LIne 16: Insert --as-- after "defined".

Signed and Sealed this

Eighth Day of August, 2006

JON W. DUDAS
*Director of the United States Patent and Trademark Office*